(12) United States Patent
Uhlig

(10) Patent No.: US 6,382,027 B1
(45) Date of Patent: May 7, 2002

(54) BRAKE PAD ASSEMBLY DAMPING AND FREQUENCY MEASUREMENT METHODOLOGY

(75) Inventor: Robert P. Uhlig, Rochester Hills, MI (US)

(73) Assignee: DaimlerChrysler Corporation, Auburn Hills, MI (US)

(*) Notice: Subject to any disclaimer, the term of this patent is extended or adjusted under 35 U.S.C. 154(b) by 0 days.

(21) Appl. No.: 09/568,600

(22) Filed: May 10, 2000

(51) Int. Cl.[7] ................................................ G01M 7/02
(52) U.S. Cl. ........................................... 73/579; 73/662
(58) Field of Search ........................... 73/579, 664, 662, 73/11.05, 121, 668

(56) References Cited

U.S. PATENT DOCUMENTS 6,014,899 A  1/2000  Uhlig et al. .................. 73/664
6,314,813 B1  11/2001  Uhlig .......................... 73/664

*Primary Examiner*—John E. Chapman
(74) *Attorney, Agent, or Firm*—Ralph E. Smith

(57) ABSTRACT

A method for measuring the vibration damping of a part. The method comprises the steps of vibrating the part with a contactless vibrator, measuring the output vibrations of the part with a contactless measuring device, determining an input frequency for testing the part, the input frequency being a frequency which uses the smallest gain to cause the part to produce vibrations having an output amplitude equal to a predetermined target amplitude, providing an input to the part with the contactless vibrator such that the part vibrates at the input frequency, simultaneously interrupting the input and using the contactless measuring device to measure as a function of time an output amplitude of vibrations in the part, and determining the rate at which the vibrations in the part are damped.

11 Claims, 2 Drawing Sheets

BRAKE PAD ASSEMBLY DAMPING AND FREQUENCY MEASUREMENT METHODOLOGY

BACKGROUND OF THE INVENTION

1. Technical Field

The present invention relates generally to a method for measuring vibration-related characteristics and more particularly to a method for measuring brake pad assembly damping and resonant frequency.

2. Discussion

A longstanding problem associated with the use of vehicle brakes is the generation of annoying noise often referred to as brake squeal. Various brake system components, such as brake rotors or drums (hereinafter collectively referred to as simply "brake rotors") and brake pad or shoe assemblies (herein after referred to as simply "brake pad assemblies"), are generally considered to be the source of a variety of such noises and associated vibrations.

In order to reduce brake noise, brake rotors and brake pad assemblies have been manufactured using materials and processes which tend to reduce the vibrations produced during braking. Such advancements have generally been directed to providing a consistent friction coefficient between the braking surfaces of the brake rotors and the brake pad assemblies, as well as controlling the frequency at which these components vibrate and their ability to damp vibrations. Typically, the greater the ability of a brake system component to damp vibrations, the less apt the part is to make undesirable noise during the operation of the vehicle.

Vehicle manufacturers and brake component manufacturers have attempted to control brake system noise by specifying a minimum amount or minimum level of vibration damping inherent in the brake system components. In the case of brake pad assemblies, damping is typically affected by the composition of the friction material (i.e., pad material) as well as the use of specific damping layers. The damping layers are typically formed from an insulating material that is secured to a brake pad backing plate via an adhesive bond to provide additional damping at critical (i.e., noise-related) frequencies. The damping performance of the insulating material is frequently dependent upon the quality of the adhesive bond.

Unfortunately, determination of the quality of brake pad and the damping layer usually involves a time consuming destructive test. Where the quality of the damping layer is analyzed, for example, the test typically requires that the insulating material be peeled off the brake pad backing plate, with the analysis being based on the amount of force exerted to remove the insulating material. While this testing appears to provide a satisfactory indication of the strength and durability of the adhesive bond between the insulating material and the brake pad backing plate, this testing only provides a crude indication of the insulating material's damping performance.

Several non-destructive testing methods have been suggested wherein an accelerometer is secured to the brake pad assembly and the brake pad is subsequently excited by the impact of a hammer. The accuracy of the results obtained through these methods, however, is compromised since the accelerometer is mounted to the brake pad assembly during the test. Specifically, the accelerometer adds mass to the area of the brake pad assembly to which it is mounted, causing the brake pad assembly to respond in a manner that is not usually consistent with its performance in a brake system. Furthermore, the repeatability of the measurements is highly dependent upon the repeatability with which the accelerometer is positioned on the brake pad assembly. Small positional variances in the placement of the accelerometer tend to cause substantial variances in the measured damping of the brake pad assembly. Additional drawbacks associated with these tests are related to the efficiency with which the sample is excited by the impact hammer and the modal density of the sample.

Accordingly, there remains a need in the art for a method to accurately and repeatably test a brake pad assembly to measure its frequency response and damping capability. Ideally, the method should be "contactless" so that issues related to the mass-loading of the sample and the efficiency with which the sample is excited can be avoided. The method should also be quick and non-destructive. Such a method would provide an accurate measure of damping and frequency response, and would permit the identification of design and process variables that affect the performance of the brake pad assembly.

SUMMARY OF THE INVENTION

It is one object of the present invention to provide a method to accurately and repeatably test a brake pad assembly to measure its resonant frequency and damping capability.

It is a more specific object of the present invention to provide a nondestructive and contactless method to measure the resonant frequency and damping capability of a brake pad assembly.

In one preferred form, the present invention provides a method for measuring the vibration damping of a part. The method comprises the steps of vibrating the part with a contactless vibrator, measuring the output vibrations of the part with a contactless measuring device, determining an input frequency for testing the part, the input frequency being a frequency which uses the smallest gain to cause the part to produce vibrations having an output amplitude equal to a predetermined target amplitude, providing an input to the part with the contactless vibrator such that the part vibrates at the input frequency, simultaneously interrupting the input and using the contactless measuring device to measure as a function of time an output amplitude of vibrations in the part, and determining the rate at which the vibrations in the part are damped.

BRIEF DESCRIPTION OF THE DRAWINGS

Additional advantages and features of the present invention will become apparent from the subsequent description and the appended claims, taken in conjunction with the accompanying drawings wherein:

DETAILED DESCRIPTION OF THE PREFERRED EMBODIMENT

Figure 1:
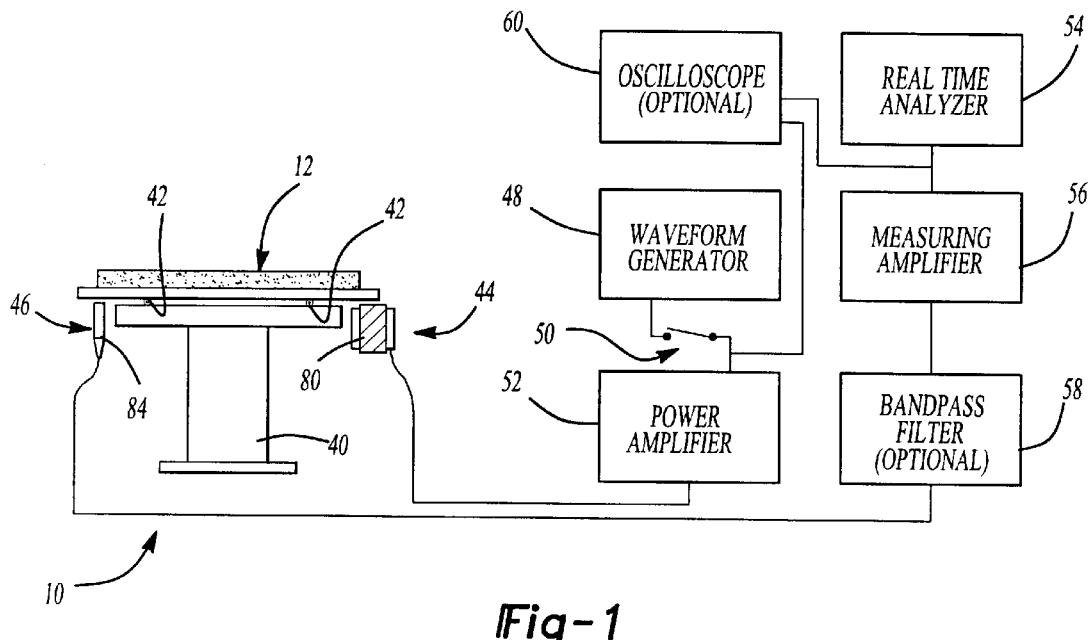
FIG. 1 is a schematic view of a test apparatus arranged in accordance with the present invention and including a block diagram of vibration signal input, output and measuring components.

With reference to FIG. 1 of the drawings, an exemplary test setup for practicing the method of the present invention is generally indicated by reference numeral 10. Test setup 10 is operable for determining the frequency response and damping rate of a test sample, such as a brake pad assembly 12.

Figure 2:
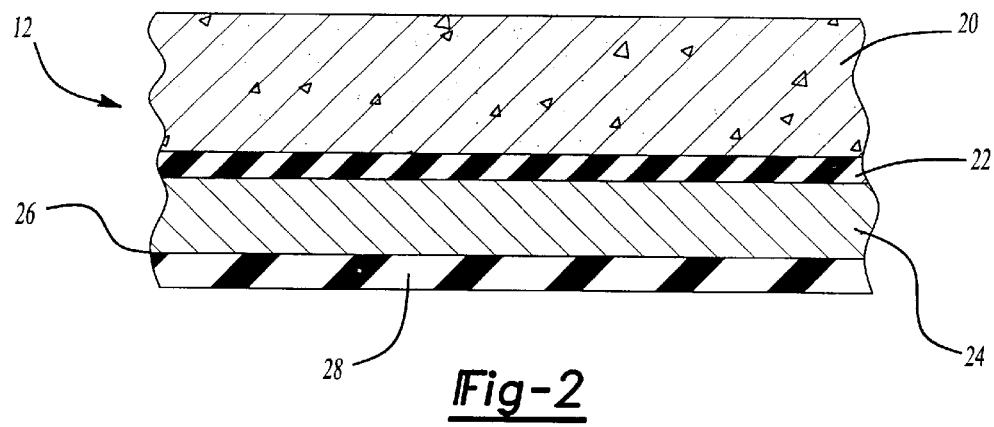
FIG. 2 is a partial sectional view of an exemplary brake pad assembly.

Brake pad assembly 12 is conventionally constructed and need not be discussed in detail. Briefly, brake pad assembly 12 is shown in FIG. 2 to include a brake pad 20, an underlayer 22, a backing plate 24, an adhesive layer 26 and an isolation member 28. Brake pad 20 is fixedly secured to backing plate 24 through conventional fasteners, such as rivets (not shown) and the adhesive character of underlayer 22. As backing plate 24 is the structural foundation of brake pad assembly 12, it is formed from a ferromagnetic material to provide sufficient strength. Alternatively, backing plate 24 may be formed from a paramagnetic material. Adhesive layer 26 and isolation member 28 are subsequently applied to the back or mounting side of the brake pad assembly 12. Isolation member 28 is configured to insulate the brake pad assembly 12 to reduce the amplitude of vibrations. Isolation member 28 may be constructed, for example, from a sheet metal material that is coated with a resilient vibration damping material. Isolation member 28 provides additional damping at critical (i.e., noise-related) frequencies.

Figure 3:
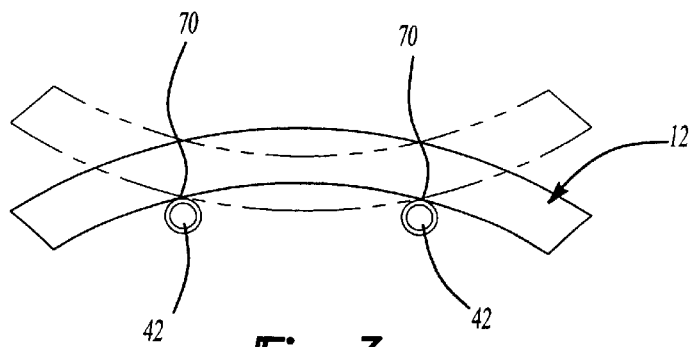
FIG. 3 is a schematic illustration of a portion of the test apparatus of FIG. 1 illustrating the brake pad assembly vibrating in its first mode of vibration.

Referring back to FIG. 1, test setup 10 is shown to include a base portion 40, a pair of resilient, vibration-isolating supports 42, a contactless vibrator 44, a contactless vibration measuring device 46, a waveform generator 48, a switch 50, a power amplifier 52, a real time analyzer 54, a measuring amplifier 56, a bandpass filter 58 and an oscilloscope 60. Supports 42 elevate brake pad assembly 12 off the surface of base portion 40. Supports 42 are spaced apart a distance equal to the distance between the nodes 70 of brake pad assembly 12. As shown in FIG. 3, the nodes 70 of brake pad assembly 12 are the points of the brake pad assembly 12 which do not move when the brake pad assembly 12 is vibrating in its first vibrational mode. Accordingly, supports may be fabricated from a non-resilient material without theoretically affecting the accuracy and repeatability of the test setup 10. However, as it is probably not possible to identically align test samples relative to the base portion 40, the use of resilient supports 42 is preferred since a resilient material will tend not to influence the test data if the sample is not positioned consistently with absolute precision.

Returning to FIG. 1, contactless vibrator 44 is positioned vertically at a predetermined spacing from the rear surface of brake pad assembly 12. In the example provided, contactless vibrator 44 is an exciter coil 80 that electromagnetically induces vibrations in brake pad assembly 12 without direct physical contact through application of a pulsing electromagnetic field that interacts with the ferromagnetic backing plate 24.

The level or amplitude of vibrations induced in brake pad assembly 12 is measured with a transducer, such as a microphone 84, which may include a preamplifier. Microphone 84 is also carefully positioned adjacent the rear surface of brake pad assembly 12 at a predetermined distance from both brake pad assembly 12 and contactless vibrator 44.

With the exciter coil 80 and microphone 84 aligned with the brake pad assembly 12 as described above, a waveform or frequency generator 48 is set to provide a sinusoidal wave output at a constant amplitude. This signal is passed through closed switch 50 to a power amplifier 52 which amplifies the output of the waveform generator 48 and sends the amplified signal to the exciter coil 80. An oscilloscope 60 may be connected to the output of the waveform generator 48 to monitor the waveform frequency.

Figure 4:
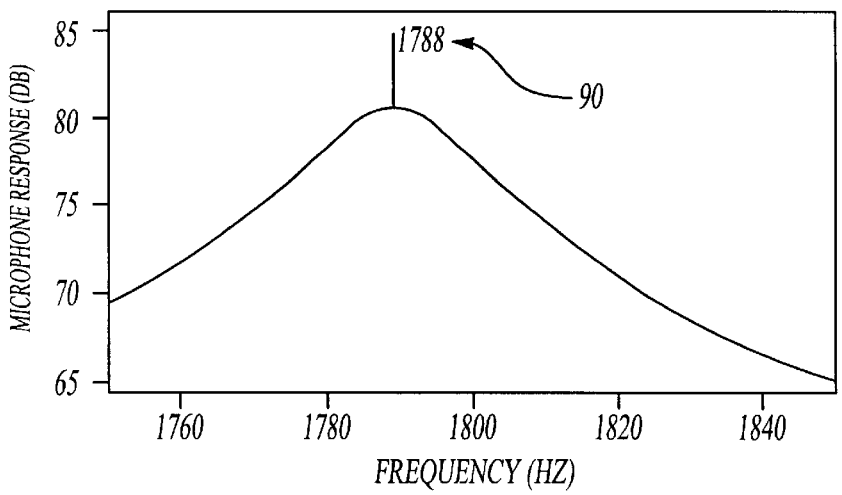
FIG. 4 is a plot depicting the relationship between frequency and amplitude for an exemplary brake pad assembly.

As the exciter coil 80 magnetically induces vibrations in the brake pad assembly 12, the microphone 84 measures the sound or vibration level emitted by the brake pad assembly 12 and provides a measure of this level to a measuring amplifier 56. A bandpass filter 58 may be used to eliminate frequencies outside the range of interest. As illustrated in FIG. 4, the output of the measuring amplifier 56 is observed as the frequency of the waveform generator 48 is varied and the frequency of peak response 90 in the brake pad assembly 12 (i.e., the initial frequency) is noted.

The waveform generator 48 is next set to a frequency that will cause the brake pad assembly 12 to vibrate at the initial frequency within a predetermined tolerance, such as 0.1 Hz, and the gain of the power amplifier 52 is adjusted such that the amplitude of the vibrations as measured by microphone 84 is approximately equal to a predetermined target amplitude. The use of a predetermined target amplitude provides a consistent basis from which the test samples are evaluated. However, as the level of power transmitted to the brake pad assembly 12 is likely to be different from the level of power transmitted to the brake pad assembly 12 during the first part of the test, the frequency of maximum response is likely to change when the power level is altered to attain the predetermined target amplitude. Consequently, it will be necessary to vary the frequency of the waveform generator 48 and the gain of the power amplifier 52 until an input frequency for testing the brake pad assembly 12 can be identified.

In identifying the input frequency, the initial frequency is first varied to determine the new frequency of peak response in the brake pad assembly 12 (i.e., updated test frequency). If the updated test frequency is different from the initial frequency, the initial frequency is set equal to the updated test frequency, the waveform generator 48 is set to vibrate the brake pad assembly 12 at the (new) initial frequency and the gain of the power amplifier 52 is adjusted such that the amplitude of the vibrations as measured by microphone 84 is approximately equal to a predetermined target amplitude. The process is then repeated until the input frequency is determined to be the frequency which uses the smallest gain to cause the brake pad assembly 12 to produce vibrations having an amplitude equal to the predetermined target amplitude.

Figure 5:
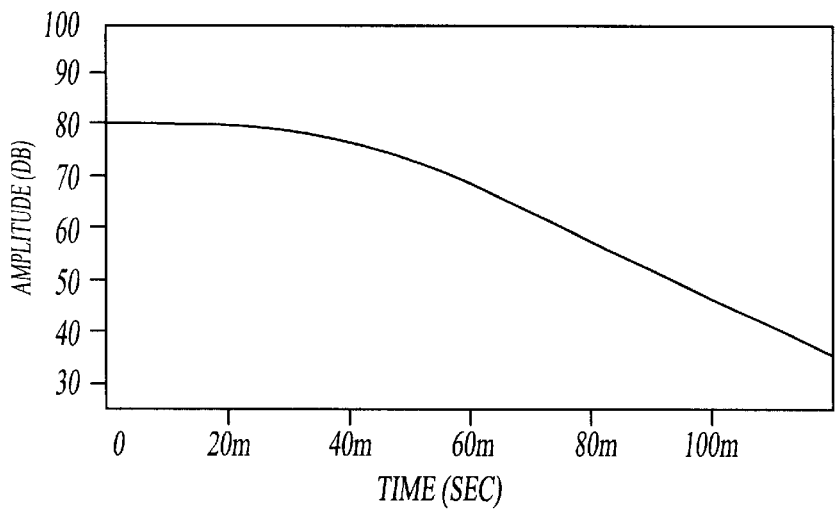
FIG. 5 is a plot of a decay curve for a first exemplary brake pad assembly obtained from the real time analyzer of FIG. 1.
Figure 6:
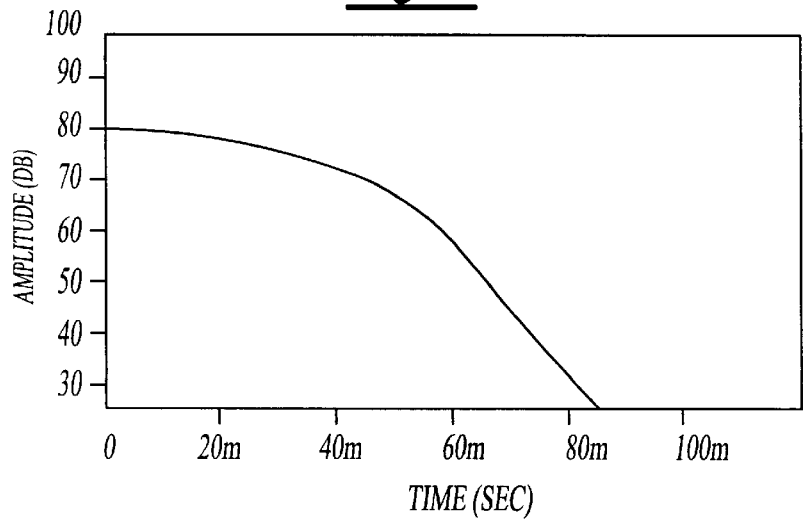
FIG. 6 is a plot of a decay curve for a second exemplary brake pad assembly obtained from the real time analyzer of FIG. 1.

Once the input frequency has been identified, the waveform generator 48 is set such that the exciter coil 80 will cause the brake pad assembly 12 to vibrate at the input frequency. The real time analyzer 54 and the waveform generator 48 are coupled to the switch 50 such that when the switch 50 is opened, the vibrational input provided by the waveform generator 48 is interrupted and the real time analyzer 54 simultaneously records the decaying amplitude of the vibrations as a function of time. Data from the real time analyzer 54 is plotted as shown in FIGS. 5 and 6, and linear regression or other curve fitting techniques are employed to determine the amount of time, td, for the vibrations to decay a predetermined amount. Preferably the predetermined amount of decay is greater than 20 dB to minimize the error in determining the decay rate.

The methodology next calculates a Q-factor for providing a relative indication of the effectiveness with which the brake pad assembly 12 damps vibration using the following formula:

$$Q=(27.3)\times(fr)\times(td)/(dB)$$

wherein fr is the frequency at which the brake pad assembly 12 responds to the input frequency (i.e., resonant frequency) as measured in Hertz, td is the amount of time in seconds for the level of the vibrations to decay a predetermined amount, and dB is the predetermined amount of decay of the vibrations as measured in decibels. While testing has shown the method of the present to provide highly repeatable results (e.g., damping repeatability within 2% and identification of resonant frequency within 0.2%), it is recommended that the test be performed at least three times and the results averaged.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

I claim:

1. A method of measuring vibration damping of a part, the method comprising the steps of:

vibrating the part with a contactless vibrator;

measuring the output vibrations of the part with a contactless measuring device;

determining an input frequency for testing the part, the input frequency being a frequency which uses the smallest gain to cause the part to produce vibrations having an output amplitude equal to a predetermined target amplitude;

providing an input to the part with the contactless vibrator such that the part vibrates at the input frequency;

simultaneously interrupting the input and using the contactless measuring device to measure as a function of time an output amplitude of vibrations in the part; and determining the rate at which the vibrations in the part are damped.

2. The method of claim 1, wherein the part includes a component formed from a material selected from the group consisting of ferromagnetic materials and paramagnetic materials, wherein the contactless vibrator includes an exciter coil spaced apart from the part and wherein the method further comprises vibrating the part with an electromagnetic field produced by the exciter coil.

3. The method of claim 1, wherein the part comprises a brake pad assembly.

4. The method of claim 1, wherein the contactless vibrator includes a waveform generator providing a signal to a power amplifier.

5. The method of claim 1, wherein the part is mounted on a pair of resilient supports, the resilient supports being arranged generally parallel to one another and spaced apart at a distance approximately equal to a distance between a pair of nodes of the part.

6. The method of claim 1, wherein the contactless measuring device includes a transducer.

7. The method of claim 1, wherein the output amplitude is measured with a microphone, wherein the period of time is measured with a real time analyzer and wherein the method further comprises measuring with the microphone a sound level of the vibrating part, plotting the sound level versus time on the real time analyzer and measuring a time, td, for a predetermined decay span, dB, after the input has been interrupted.

8. The method of claim 7, further comprising the step of computing a value Q for the part wherein $$Q=(27.3)\times(fr)\times(td)/(dB)$$

wherein fr is the frequency at which the test sample responds to the input frequency as measured in Hertz, td is measured in seconds and dB is measured in decibels.

9. The method of claim 8, wherein the predetermined decay span is at least 20 dB.

10. The method of claim 1, wherein the step of determining an input frequency for testing the part includes the steps of:

determining an initial test frequency;

providing an initial input to the part with the contactless vibrator, the initial input causing the part to vibrate at the initial test frequency;

measuring the output amplitude of the vibrations in the part;

determining if the output amplitude of the vibrations in the part is equal to the predetermined target amplitude; and if the output amplitude of the vibrations in the part is not equal to the predetermined target amplitude, altering the amplitude and frequency of the initial input and repeating the above two steps.

11. The method of claim 10, wherein the step of altering the initial input comprises the steps of:

varying the initial test frequency while measuring the output amplitude of the vibrations in the part to identify an updated test frequency;

setting the initial input to correspond to the updated test frequency;

providing the initial input to the part with the contactless vibrator, the initial input causing the part to vibrate at the initial test frequency;

measuring the output amplitude of vibrations in the part;

if the output amplitude does not equal the predetermined target amplitude, adjusting the gain of the initial input such that the output amplitude of the vibrations in the part is equal to the predetermined target amplitude; and repeating each of the above steps until the input frequency is the frequency which uses the smallest gain to produce vibrations in the part having an amplitude that is equal to the predetermined target amplitude.

* * * * *